United States Patent [19]

Mjos et al.

[11] 4,034,072

[45] July 5, 1977

[54] SERUM HEPATITIS TEST

[75] Inventors: Shirley A. Mjos, Millis; Roger N. Piasio, Medfield, both of Mass.

[73] Assignee: Corning Glass Works, Corning, N.Y.

[22] Filed: July 21, 1975

[21] Appl. No.: 597,359

[52] U.S. Cl. .............................. 424/1; 23/230 B; 424/1.5; 424/12

[51] Int. Cl.$^2$ ................ G01N 33/00; A61K 39/00; G21H 5/02

[58] Field of Search .............. 424/1.5, 12; 23/230 B

[56] References Cited

UNITED STATES PATENTS

| | | |
|---|---|---|
| 3,555,143 | 1/1971 | Axen et al. ......................... 424/1.5 |
| 3,652,761 | 3/1972 | Weetall .............................. 424/12 |
| 3,867,517 | 2/1975 | Ling ................................... 424/1 |

OTHER PUBLICATIONS

Weetall, Biochem. Journal, vol. 117, 1970, pp. 257–261.

Bodley et al., steroids, vol. 21, No. 1, Jan. 1973, pp. 1–16.

Leonard et al., Radioimmunoassay and Related Procedures in Medicine, vol. II, Viena, 1974, pp. 367–375.

*Primary Examiner*—Benjamin R. Padgett
*Assistant Examiner*—Christine M. Nucker
*Attorney, Agent, or Firm*—James A. Giblin; Clinton S. Janes Jr.; Clarence R. Patty, Jr.

[57] ABSTRACT

Reagent and method for detecting the presence of hepatitis associated antigen (HAA) in blood serum. The reagent comprises anti-HAA antibodies coupled via an intermediate silane to a plurality of siliceous particles having a surface area of at least about 1 m$^2$/g and, if the particles are porous, an average pore diameter of at least about 1000 A. The test method comprises the steps of incubating a serum sample with the reagent to complex any HAA in the sample with the antibodies of the reagent, incubating the reaction product with a solution of radio labelled anti-HAA antibodies to complex the labelled antibodies with any HAA that may be complexed to the reagent, separating the incubation products from the solution of labelled antibodies, and counting the radioactivity of either the separated products or the remaining solution to determine whether HAA was in the sample.

14 Claims, No Drawings

SERUM HEPATITIS TEST

BACKGROUND OF THE INVENTION

Field

This invention relates generally to the field of radioassays and specifically to a reagent and method for detecting the presence of hepatitis in a sample of human blood serum.

Very broadly, the term radioassay refers to the use of radioactively labelled (tagged) substances to determine the concentration or presence of a substance in a fluid. Typically, radioassays are used to determine very small amounts of a given substance. The term radioimmunoassay (RIA) refers to the use of tagged substances in an antibodyantigen reaction to determine the presence or concentration of either substance. A typical RIA for a given substance (against which there are available antibodies) is based on the observation that a known amount of that substance (labelled) will tend to compete with an unknown amount of that substance (unlabelled) for a limited number of complexing sites on the antibodies. Hence, by counting the radioactivity of the products of such reaction, it is possible to determine an unknown concentration.

An essential step in RIA is the separation of immunochemically complexed products from the incubation solution. Ideally, the separation should be complete, relatively simple, and quick. It has been recognized that separation is greatly facilitated by using antibodies or antigenic substances which have been immobilized by attachment to essentially water-insoluble carrier materials. When such carrier materials are used in RIA, the technique is commonly referred to as solid phase RIA or SPRIA. The present disclosure is concerned with a SPRIA useful in detecting the presence of hepatitis associated antigen (HAA) in human blood serum.

Prior Art

It is well known that antibodies and antigenic substances can be immobilized by chemical attachment to a wide variety of carriers. Such attachments to organic carrier are described, for example, in U.S. Pat. No. 3,555,143, to Axen et al. Methods of attaching antibodies via intermediate silane coupling agents to inorganic materials are described in U.S. Pat. No. 3,652,761 to Weetall. More recently, in U.S. patent application Ser. No. 447,252, filed Mar. 1, 1974 in the names of W. Vann et al., entitled "Solid Phase Radioimmunoassay", and assigned to the present assignee, there are disclosed in detail SPRIA methods for determining concentration of digoxin, insulin, and estriol. Antibodies which can complex with those substances are coupled via silanes to porous glass particles having particle sizes ranging in the mircron and sub-micron range.

Although the technology for employing SPRIA techniques to test for NAA (hepatitis) has been available for some time, surprisingly, the commercialization of that technology has been rather limited. See, for example, the relatively recent summary entitled "Radioassay Test Kits and Components", Laboratory Management, September 1974, pp. 29 –42. See also, recently issued U.S. Pat. No. 3,867,517 to Chung-Mei Ling which discloses a solid phase technique for detecting HAA. That disclosure employs a so-called "Sandwich" technique for detecting HAA in which HAA is sandwiched between an immobilized anti-HAA antibody and a tagged anti-HAA antibody. In one embodiment, the untagged antibodies are immobilized by attachment to the inner surfaces of a test tube.

We have found that by carefully combining certain features of the above disclosures with our own discovery, a very sensitive and relatively quick test for HAA is possible. Detailed descriptions of our reagents and methods are given below.

SUMMARY OF THE INVENTION

Our reagent for detecting the presence of HAA in a blood serum sample comprises a composite consisting of anit-HAA antibodies covalently bonded via intermediate silane coupling agents to a plurality of essentially siliceous particles having a surface area of at least about 1 $m^2$/g and, if the individual particles are porous, an average pore diameter of at least about 1000 A. Our test method comprises the following steps:

a. incubating a serum sample with the reagent under conditions sufficient to complex any HAA in the sample with the anti-HAA antibodies of the reagent;

b. separating the reagent from the incubation medium of (a);

c. incubating the separated reagent with a solution of radiolabelled anti-HAA antibodies under conditions sufficient to complex the radiolabelled antibodies to any HAA complexed to the anti-HAA antibodies of the reagent;

d. separating the reaction product of step (c) from the solution; and e. measuring the radioactivity of the separated reaction product or the remaining solution to determine whether HAA was present in the serum sample.

In preferred embodiments the reagent is in the form of an aqueous suspension comprising about 10 to 300 micrograms ($\mu$g) of composite per test in 0.1 to 0.2 ml of water and the antibodies are coupled to silica or porous glass particles having an average particle size ranging from about 0.1 to about 10.0 microns, preferably about 0.1 to 3 microns. The preferred serum sample ranges from about 100 $\lambda$ to about 1000 $\lambda$ and the initial incubation is for a period of at least about 5 minutes. The second incubation is preferably with $I^{125}$-labelled anti-HAA antibodies having a radioactivity count of at least about 20,000 cpm.

SPECIFIC EMBODIMENTS

The essential reagent for our test is a composite which can be represented as G-S-Ab where G represents an essentially siliceous particle such as a silica or porous glass particle, S represents a silane coupling agent having a silicon functional group (attached to the surface of G by known means) and an organofunctional group which can be modified for covalent coupling to Ab, an anti-HAA antibody. The actual attachment of the Ab through the S to the G is not considered a part of this invention. See, for example U.S. Pat. No. 3,652,761 to H. H. Weetall. However, the physical and chemical properties of the carrier G are very important for ultimate assay sensitivity and speed.

The physical limitations of the carrier can be appreciated by considering the use of the carrier in an actual assay. The starting material (reagent) is represented by G-S-Ab. This reagent is incubated with an unknown serum sample. If HAA is present, the complex represented as G-S-Ab.HAA can form, the HAA being immunochemically complexed to the Ab of the reagent. After this initial incubation, the reaction product G-S-Ab.HAA is incubated with a solution of the tagged antibodies (Ab*) to form the reaction product G-S-Ab.HAA.Ab*, the Ab* (e.g., I$^{125}$-labelled anti-HAA) being immunochemically complexed with the HAA. It can be appreciated that the accuracy of any test for HAA presumes an essentially complete separation of the above reaction product from the solution of tagged antibodies. Such separation is assured by choosing a carrier particle size large enough to be centrifuged out with conventional centrifuges found in a clinical laboratory. To accomplish such separation, the minimum average particle size should be at least about 0.1 microns.

Because of the size of the various complexes formed, consideration of carrier surface area and porosity are very important. For example, as a general rule, a large surface area permits a relatively high loading of Ab and, ultimately, a relatively sensitive assay. It is well known that surface area can be increased by comminuting particles and/or providing porous particles. However, for our reagent, there is a practical lower limit to the average pore size permissible because of the very size of the complex products and diffusional requirements. As a very practical matter, we have found that the minimum surface area of our carrier should be at least about 1 m$^2$/g. This surface area can be obtained by either comminution down to an average particle size within the range of about 0.1 to 10 microns or by using carefully defined porous particles.

The size of the "sandwich" complex of our assay is about 1 × 10$^6$ Daltons. Through a series of experiments, we have found those physical properties for the carrier which can be deemed minimum practical requirements. For example, to accomodate the complexes and permit diffusion of reactants, the average pore diameter of the carriers (if porous) should be at least 1000 A. This minimum pore size can be obtained, for example, in 200 to 400 mesh particles. However, particles of such sizes will not remain in suspension for prolonged periods. Hence, an assay using those particles as carriers would be done in a column application or in a batch mode with agitation. In a preferred method, the assay is done with a suspension of carrier particles having an average particle size in the micron range. However, as the average particle size decreases, the range of useable pore sizes (>1000 A) also decreases. Hence the carriers for our assay have physical properties which result from a unique interrelationship of complex sizes, diffusional requirements, separation requirements, surface area requirements and minimum pore size requirements.

We have found, for example, that porous glass particles having an average particle size of 1 to 3 microns and an average pore diameter of 550 A are not an efficient carrier because the majority of the relatively large suface area is contributed by the pores which are too small to accomodate the 1 × 10$^6$ Dalton complex. On the other hand, 0.1 to 0.4 (average particle size) "porous" glass comminuted from 550 A stock can be used quite successfully because the available surface area is contributed primarily by the surface and not by internal pores. At the other extreme of surface area, we have shown that non-porous particles of about 200 to 400 mesh are not practical carriers because of the minimal surface area.

As a practical matter, our best carriers to date are non-porous and have an average particle size ranging from about 1 to 3 $\mu$. These particles provide sufficient surface area for high loading (and assay sensitivity); they can be put into suspension for optimum diffusion of reactants during incubation periods; and they are relatively easy to handle. The mean particle size (2 $\mu$) provides a surface area of about 7 m$^2$/g, well above the minimum requirement of at least about 1 m$^2$/g. Non-porous particles having an average particle size of 5 to 10 $\mu$ (surface area about 3 m$^2$/g) also worked as carriers, but not as well as the 1-3 $\mu$ carriers. An average particle size of about 10$\mu$ appears to be the largest practical for non-porous carrier useful in our assay.

Below is a table showing the various combinations of surface areas, average pore sizes and particle sizes of the siliceous carriers we have used. Also shown is a summary of overall assay results using the each carrier with − meaning the carriers were not practical and where + and ½+ indicate the carriers were very practical or somewhat (borderline) practical, respectively. In the table below, the porous silica consisted of porous glass particles described in detail below. The other carriers were non-porous silica, as indicated.

TABLE I

| Carrier Properties | | | | |
|---|---|---|---|---|
| Surface Area (m$^2$/g) | Particle Size (Avg.) | Porous (Yes/No) | Pore dia. (Avg., Å) | Assay Results |
| unk | 1-3$\mu$ | yes | 550 Å | − |
| >300 | 2-5$\mu$ | yes | 250 Å | − |
| 0.6 | 200/400 mesh | no | − | − |
| ~3 | 5-10$\mu$ | no | − | ½+ |
| >100 | 0.1-.4$\mu$ | yes | "550" | + |
| ~8 | 1-3$\mu$ | no | − | + |
| unk | 5-10$\mu$ | yes | 1500 | + |
| unk | 200/400 mesh | yes | 2500 | + |

From our experiments, it can be concluded that the carriers should have a surface area of at least about 1 m$^2$/g, a particle size of at least about 0.1 and, if porous, an average pore diameter of at least about 1000 A. obtaining the above requirements is assured by using essentially siliceous starting materials having surface oxide or hydroxyl groups capable of reaction with the silicon functional portion of the silane coupling agent. Such siliceous materials are available commercially (e.g. Syloid porous silica, CPG controlled pore glass). Porous glass can be made, for example, according to the teachings of U.S. Pat. No. 3,549,524. Typically porous glass has an average pore diameter ranging from about 100 to 2500 A although, as indicated above, we have found the working range of porous glass has an average pore diameter of about 1000 A to about 2500 A.

In very preferred embodiments, the siliceous particles, whether non-porous or porous, should have a minimum average particle size of about 0.1$\mu$ to permit convenient centrifugation and a maximum average particle size of about 3$\mu$ to permit suspension in an aqueous medium for optimum reaction and diffusion of reactants.

PREPARATION AND USE OF REAGENTS

The preparation of the composite used in the reagent involves two basic steps. In the first step, the particles are reacted with a silane coupling agent to provide an organic base for coupling the antibodies. Prior to the silanization step, care must be taken to assure that the particles are clean and have available surface oxide or hydroxyl groups available for bonding with the silicon-functional portion of the silane. Such cleaning, if even necessary, can be accomplished by known methods. After reaction with the silane, the carrier is referred to as silanized. Alternatively, the silanized carrier is described with reference to the organofunctional group at the carrier surface. For example, when controlled pore porous glass (CPG) particles are reacted with a silane having an arylamine or alkylamine organo-functional portion, the particles can be referred to, respectively, as arylamine CPG or alkylamine CPG. Detailed methods for silanizing inorganic particles can be found in U.S. Pat. No. 3,519,538 issued to Messing et al. (for coupling enzymes); U.S. Pat. No. 3,652,761 issued to Weetall (antibodies and anitgens); and U.S. Pat. application Ser. No. 447,252, cited above (antibodies). Once silanized, the organofunctional portions of the silane are commonly modified for coupling to the antibodies.

After silane modifications (e.g., diazotization), the anti-HAA antibodies are reacted in a solution with the modified silanized carriers under conditions sufficient to assure maximum bonding of the antibodies in an active (functioning) state. It is thought that the anti-HAA anti-bodies retain their complexing ability with a variety of coupling reactions. As a general rule, to assure maximum antibody loading, the amount of antibody reacted with the modified silanized carrier is in the range of about 100λ to 1 ml. of unfractionated antibody serum for each gram of carrier, on a dry weight basis.

After the antibodies are immobilized on the carriers, the resulting composites are preferably put in an aqueous suspension (e.g., by sonication) for use. Our preferred suspension for a single test consists of about 10μg to 300μg of composite per 0.1 to 0.2 ml of aqueous solution, preferably buffered with 0.03 M phosphate buffered saline to maintain a pH of about 6.5 to 8.0. The reagent for an individual test for serum hepatitis consists of the composite in an aqueous suspension, the suspension being contained in an individual test tube which is stoppered until use.

To perform the test (for example, with an individual unit tube), about 200λ of the sample human blood serum is added to the suspension (about 200λ) and allowed to incubate, preferably at 45° C for about 10 minutes. If HAA is present in the serum sample, it will complex with the immobilized anti-HAA antibodies. After incubation, the resulting composites, if HAA was present, can be represented as G - S - Ab.HAA where G is the siliceous carrier, S the silane, Ab is the anti-HAA antibody, and HAA is complexed thereto.

The composite is then washed, for example, by centrifuging the particles out of the incubation medium and then resuspending in a wash solution and again centrifuging out. One wash is generally sufficient to assure a composite essentially free of extraneous matter such as serum proteins or excess antigen.

After the wash, the composite can be represented as either

G - S - Ab.HAA or

G - S - Ab depending on the serum sample. The composite is then separated. Then, about a 200λ solution of labelled anti-HAA antibodies are added and allowed to incubate with the suspension, preferably for about 20 minutes at about 45° C. Since HAA can complex with more than one anti-HAA antibody, the following complex will form if HAA was present in the serum sample.

G - S - Ab.HAA.Ab*, where Ab* represents a radiolabelled anti-HAA antibody. Our preferred antibodies are labelled with $I^{125}$. It should be understood that the above representation are illustrative only and that the actual bonding and complexing reactions are not as simplistic as the illustrations indicate.

After the above incubation with the tagged antibodies, the solid phase incubation products are separated from the incubation medium by, for example, centrifugation at 2000 rpm for 1 minute. Then, the separated composites or the remaining medium is counted for radioactivity to determine if HAA was present in the serum sample. To allow for trace residual tagged material and background noise, the test should be done with negative and positive controls to have a basis for interpreting the counts. As a general rule, the ratio of counts (mean) of the positive controls to negative controls should be at least about 3:1. In interpreting the test results counts, a very high ratio of sample counts to negative control counts is desirable to indicate a clear positive in the test. Even though a serum hepatitis test only requires a positive or negative result, it can be appreciated that a highly positive result is more desirable and informative than a "borderline" positive which might have to be confirmed.

In our experiments, we coupled anti-HAA antibodies to different siliceous particles having both particle sizes and pore sizes within the range required for suspendability and/or test sensitivity.

Approximately 2 to 3 gram batches of reagents were prepared using the carriers described above. Our preferred reagents were made by silanizing the carriers with α-am silane (A-1100, Union Carbide) to form an arylamine surface which is subsequently modified by known means to yield a highly reactive diazotized surface capable of reacting with a solution of the anti-HAA antibodies. About one ml of crude antibody serum is reacted with each gram of diazotized carrier to yield a composite G-S-Ab having the Ab coupled via azo linkages. In our studies below, the very preferred carrier consisted of fused silica particles which were non-porous and had an average particle size of 1 to 3 microns.

The utility of our preferred reagent is shown in the experiments below where the suspension of reagent was used to "detect"or confirm the presence of HAA in blood samples or from a commercially available kit. In considering the data below, it should be stressed that a test for HAA can be considered successful if the ratio of counts (cpm) of a positive sample to a known negative control is at least 3:1. As shown below, we were able to exceed this ratio with our reagent suspension.

Titering procedures for both our HAA samples and anti-HAA antibody are shown below and compared to the results obtained via CEP methods.

TABLE II

Titering Procedure for HAA Antigen

To titer the hepatitis antigen used, we made serial dilutions of the antigen in PBS/BSA buffer.

| Dilution | (−) CPM | (+) CPM | |
|---|---|---|---|
| ntrols | 210 | 787 | (1:1000 CEP) |
|  | 278 | 778 |  |
| :0 |  | 13109 |  |
|  |  | 13228 |  |
| :00 |  | 111509 |  |
|  |  | 11163 |  |
| :000 |  | 4476 |  |
|  |  | 4376 |  |
| :0,000 |  | 1179 |  |
|  |  | 1192 |  |
| :00,000 |  | 359 |  |
|  |  | 426 |  |

TABLE III

Titering Procedure for anti-HAA Antibody

After sample incubation and wash, we added serial lutions of antibody and incubated for 30 minutes, ished, centrifuged, and aspirated.

|  | (−) | (+) |
|---|---|---|
| ntrols | 190 | 1200 |
|  | 201 | 1190 |
| 0 | 209 | 201 |
|  | 190 | 189 |
| 00 | 273 | 220 |
|  | 216 | 215 |
| 1000 | 199 | 305 |
|  | 181 | 291 |
| 10,000 | 111 | 491 |
|  | 210 | 501 |
| 100,000 | 101 | 1100 |
|  | 290 | 1200 |

From the above titering experiments, the titer of the et antibody solution was found to be 1:10,000. This is e highest dilution which completely prevents binding the tagged antibody to the antigen.

TABLE IV

HAA Incubation Time Studies he immobilized hepatitis antibody (100–300 μg of omposite in 100λ of PBS-BSA buffer) was incubated ith 0.2 ml serum samples at 40° C. from 10 minutes to hours. After incubation, the samples were washed ice, and 0.2 ml I-125 hepatitis antibody were added id incubated for 30 minutes at 45° C. The sample was ashed two times and counted.

| Antigen Incubation Time | (−) CPM | (+ 1:1000CEP) CPM |
|---|---|---|
| 10 minutes | 550 | 2363 |
|  | 400 | 2100 |
| 30 minutes | 515 | 2497 |
|  | 518 | 2561 |
| 60 minutes | 605 | 2301 |
|  | 519 | 2675 |
| 120 minutes | 563 | 2738 |
|  | 482 | 2269 | om the above experiments, it can be seen that the g–Ab reaction is over in about 10 minutes.

TABLE V

Varying Sample Size for Increased Sensitivity

Experiments were done to determine the efficiency the test when sample size is changed. Positive sames used were a 1:500 dilution of a CEP control obined commercially.

| Sample Size (λ) | (−) CPM | (+) CPM |
|---|---|---|
| 100 | 206 | 586 |
|  | 267 | 488 |
| 200 | 201 | 783 |
|  | 302 | 894 |
| 300 | 194 | 1217 |
|  | 199 | 1112 |
| 400 | 204 | 1212 |
|  |  | 1210 |

For marginal positive samples, the sample can be retested with increased sample size, as indicated above.

From the above experiments, it can be seen that our reagent permitted a relatively rapid detection (+:− ratio > 3:1). Our initial incubation was over in about 10 minutes. Our total test time can be as low as 30 minutes. Present tests take about 3 hours.

Since the above described reagents and methods can be modified, it is intended that the scope of our invention be limited only the claims.

We claim:

1. A method of detecting the presence of hepatitis associated antigen in an unknown serum sample, the method comprising the steps of:
   a. incubating the serum sample with a reagent comprising anti-hepatitis associated antigen antibodies covalently bonded via an intermediate silane coupling agent to a plurality of essentially siliceous particles having a surface area of at least about 1 $m^2/g$ and, if porous, an average pore diameter of at least about 1000 A, the incubation being under conditions sufficient to allow complexation of any hepatitis associated antigen in the sample with the anti-hepatitis associated antigen antibodies of the reagent;
   b. separating the reagent from the incubation medium of step (a);
   c. incubation the separated reagent with a solution of radio labelled anti-hepatitis associated antigen antibodies under conditions sufficient to complex the labelled antibodies with any hepatitis associated antigen complexed to the antibodies of the reagent;
   d. separating the reaction products of step (c) from the solution; and
   e. measuring the radioactivity of the separated products or the remaining solution to determine whether hepatitis associated antigen was present in the serum sample.

2. The method of claim 1 wherein the siliceous particles of step (a) are non-porous and have an average particle size of about 1 to 3 microns.

3. The method of claim 1 wherein the reagent is in the form of an aqueous suspension comprising about 10 to 300 micrograms per 0.1 to 0.2 ml of water.

4. The method of claim 1 wherein the first incubation is for a period of about 5 to about 10 minutes.

5. The method of claim 1 wherein the antibody of step (c) is labelled with $I^{125}$.

6. The method of claim 5 wherein the solution of labelled antibody has a count of at least 20,000 cpm.

7. A method of determining the presence of hepatitis associated antigen in a serum sample, the method comprising the steps of:
   a. reacting the sample with an aqueous suspension of a composite represented by G - S - Ab where G represents a siliceous particle having a size ranging from about 0.1 to about 10 microns, S represents a silane coupling agent having a silicon functional portion attached to G and an organofunctional portion attached to Ab, and Ab is an anti-hepatitis associated antigen antibody, the reaction being under conditions sufficient to complex any hepatitis associated antigen in the serum sample with the Ab of the composite;

b. removing the composite from the reaction medium;

c. reacting the composite with a solution of radioactively labelled anti-hepatitis associated antigen antibodies under conditions sufficient to complex the antibodies with any hepatitis associated antigen complexed to the Ab of the composite;

d. separating the composite from the solution of step (c); and e. counting the radioactivity of the separated composite or the remaining solution and using that count to determine whether hepatitis associated antigen was in the serum sample.

8. The method of claim 7 wherein the siliceous particle has a size ranging from about 0.1 to about 3.0 microns.

9. The method of claim 7 wherein the aqueous suspension of step (a) comprises about 10 to 300 micrograms of composite per 0.1 to 0.2 ml of water.

10. The method of claim 7 wherein the radiolabelled antibody step (c) is labelled with $I^{125}$.

11. A reagent for determining the presence of hepatitis associated antigen in a blood serum, the reagent comprising anti-hepatitis associated antigen antibodies covalently bonded via intermediate silane coupling agents to essentially siliceous particles having an average particle size ranging from about 0.1 to about 10 microns.

12. The reagent of claim 11 wherein the particles exist in an aqueous suspension.

13. The reagent of claim 12 wherein the suspension comprises about 10 to 300 micrograms per 0.1 to 0.2 ml of water.

14. The reagent of claim 11 wherein the particles have an average particle size ranging from about 1.0 to about 3.0 microns.

* * * * *